US005858693A

United States Patent [19]

Cottingham

[11] Patent Number: 5,858,693

[45] Date of Patent: Jan. 12, 1999

[54] DEVICE AND METHOD FOR PHAGE-BASED ANTIBIOTIC SUSCEPTIBILITY TESTING

[75] Inventor: Hugh V. Cottingham, Caldwell, N.J.

[73] Assignee: Becton Dickinson and Company, Franklin Lakes, N.J.

[21] Appl. No.: 883,722

[22] Filed: Jun. 27, 1997

Related U.S. Application Data

[62] Division of Ser. No. 480,807, Jun. 7, 1995, abandoned.

[51] Int. Cl.[6] .............................. C12Q 1/66; C12Q 1/00; C12Q 1/18

[52] U.S. Cl. .................................... 435/8; 435/4; 435/32; 435/5; 436/149; 436/63

[58] Field of Search ................................. 435/8, 4, 32, 5; 436/149, 63

[56] References Cited

U.S. PATENT DOCUMENTS 4,935,147 6/1990 Ullman et al. .............................. 435/4

5,076,950 12/1991 Ullman et al. .............................. 435/4

*Primary Examiner*—Louise N. Leary

*Attorney, Agent, or Firm*—David W. Highet, Esq.

[57] ABSTRACT

A phage-based antibiotic susceptibility test is carried out by maintaining a patient sample in a sealed sample well during addition of the phage and Luciferin substrate used in the test, in order to prevent contamination of the laboratory environment. The phage is adhered in dried form to a metal carrier disk which is retained beneath the cap of the sealed sample well by means of an external magnet, and is mixed with the patient sample by removing the external magnet and allowing the carrier disk to fall to the bottom of the sample well. The Luciferin substrate is adhered to the underside of the cap and is mixed with the patient sample by shaking or inverting the sealed sample well after the metal carrier disk has separated from the underside of the cap. A row of connected sample wells and caps may be employed to allow the same patient sample to be tested with multiple antibiotics.

3 Claims, 10 Drawing Sheets

DEVICE AND METHOD FOR PHAGE-BASED ANTIBIOTIC SUSCEPTIBILITY TESTING

This is a division of application Ser. No. 08/480,807, filed Jun. 7, 1995 now abandoned.

FIELD OF THE INVENTION

The present invention relates generally to devices and methods for carrying out biological processes on liquid biological samples, and is particularly concerned with devices and methods for testing the susceptibility of bacteria in patient samples to antibiotics using phage-based techniques while maintaining the samples in sealed sample wells to prevent contamination.

BACKGROUND OF THE INVENTION

The diagnosis of a bacterial disease is only the first step in its treatment and cure. Due to the existence of drug-resistant forms of many types of bacterial diseases, it is sometimes necessary to perform further tests in order to determine which antibiotic, among all of those known to be effective against the disease in question, will be effective for the particular patient and bacterium involved. Typically, these additional tests are carried out using culture methods. The various antibiotic agents are individually cultured with a patient sample, and the antibiotic which most effectively kills the bacteria is then elected for use in treating the patient.

While culture methods are useful in determining which antibiotic will be effective, they are very time-consuming, requiring as much as twelve weeks to determine antibiotic susceptibility. The resulting delay in beginning treatment can allow the disease to progress further, sometimes to the point where the patient dies. Recently, a new method has been developed which reduces the time necessary to determine antibiotic susceptibility to as little as two days. This method, which is disclosed in U.S. Pat. No. 4,861,709 to Ulitzur et al incorporated herein by reference, uses a specific bacteriophage which has the ability to infect the disease-causing bacteria. The phage causes the infected bacteria to produce an enzyme known as Luciferase. Luciferase is a well-known enzyme which, when combined with the substrate Luciferin, causes the substrate to emit light. In a phage-based test for antibiotic susceptibility, a patient sample is cultured individually with each antibiotic for a day or two. The phage is then added to the sample and incubated for a few hours, after which the Luciferin substrate is added. The sample is then observed for the presence of luminescence. If luminescence is present, the bacteria are still alive and the antibiotic with which they were initially cultured was not effective against them. If there is no observed luminescence, the bacteria are dead and the antibiotic with which they were initially cultured was effective against them.

Because phage-based antibiotic susceptibility tests are performed on patient samples containing live bacteria, they are dangerous to handle and special precautions must be observed. The addition of phage and Luciferin to the sample, and transfers of the sample between different containers, must be carried out in isolation from the general laboratory environment. These requirements have kept the phage-based antibiotic susceptibility testing method from wide acceptance. Presently, it is not possible to add the phage, and subsequently the Luciferin substrate, to the patient sample without opening the culture plate or test tube in which the sample is contained.

It is therefore an object of the present invention to provide an apparatus which contains all of the elements necessary for carrying out phage-based antibiotic susceptibility testing.

It is another object of the invention to provide an apparatus which can be used to sequentially add phage and Luciferin, at different times, to a patient sample or antibiotic culture while remaining sealed.

It is a further object of the invention to provide an apparatus which will allow gas transfer with the ambient environment while remaining sealed to bacteria.

It is a still further object of the invention to provide an apparatus which will permit instrumented detection of luminescence while sealed.

It is a still further object of the invention to provide an apparatus or device which can be used to sequentially add phage and Luciferin, at different times, to multiple patient samples or antibiotic cultures while remaining sealed.

It is yet another object of the invention to provide a method for carrying out phage-based antibiotic susceptibility tests, and other types of biological and non-biological processes, on liquid samples while the samples are contained in sealed sample wells.

SUMMARY OF THE INVENTION

In accordance with the present invention, the disadvantages and limitations of the prior art are substantially avoided by providing an apparatus and method in which magnetic force is used to add a reagent to a liquid biological sample while the sample is contained in a sealed sample well. In a preferred embodiment of the invention, two different reagents can be added to the liquid biological sample in the sealed sample well at different times. The present invention finds particular utility in phage-based antibiotic susceptibility testing, but is also applicable to other types of biological and non-biological processes.

In one aspect, the present invention is directed to an apparatus for carrying out a biological process on a liquid biological sample. The apparatus comprise a sample well for containing a liquid biological sample, with the sample well having a top opening for admitting the liquid biological sample into the sample well and a bottom portion below the top opening in which the liquid biological sample is held. A cap is receivable by the sample well for sealing the top opening after a liquid biological sample has been admitted into the sample well. A first member is removably held in proximate contact with an outside surface of the cap, and a second member is held in proximate contact with an inside surface of the cap by magnetic attraction to the first member. The second member carries a reagent to be added to the liquid biological sample during the biological process. Removal of the first member from the cap causes the second member to separate from the inside surface of the cap and fall into the bottom portion of the sample well, thereby allowing mixing between the reagent and the liquid biological sample while the sample well remains sealed by the cap. In a preferred embodiment of the invention, a second reagent is carried by an inside surface of the cap and is substantially covered by the second member when the second member is in proximate contact with the underside of the cap. In this embodiment, separation of the second member from the cap by removal of the first member from the cap exposes the second reagent for mixing with the liquid biological sample by shaking or inverting the sealed sample well.

In another aspect, the present invention is directed to an apparatus for carrying out biological processes on a plurality of liquid biological samples. The apparatus comprises a plurality of connected sample wells for containing a corresponding plurality of liquid biological samples, with each of the sample wells having a top opening for admitting the liquid biological sample into the sample well and a bottom portion below the top opening in which the liquid biological sample is held. The apparatus also includes a plurality of connected caps that are receivable by the sample wells for sealing the top openings after liquid biological samples have been admitted into the sample wells. A first member is removably held in proximate contact with the top outside surfaces of the plurality of connected caps, and plurality of second members are held in proximate contact with the undersides of the top outside surfaces of the respective caps by magnetic attraction to the first member. Each of the second members carries a reagent to be added to the liquid biological sample in the corresponding one of the plurality of connected sample wells. Removal of the first member from the plurality of connected caps causes each of the second members to separate from the inside surface of the respective cap and to fall into the bottom portion of the respective sample well to allow mixing between the reagents and the liquid biological samples while the sample wells remain sealed by the caps.

In a further aspect, the present invention is directed to a method for carrying out a biological process on a liquid biological sample. The method comprises the steps of placing the liquid biological sample into a first portion of a sample well; placing a reagent into a second portion of the sample well located above the first portion without contact between the reagent and the liquid biological sample; sealing the sample well with the liquid biological sample and reagent therein; retaining the reagent in the first portion of the sealed sample well by magnetic force; and releasing the magnetic force to allow the reagent to fall into the second portion of the sealed sample well and mix with the liquid biological sample.

BRIEF DESCRIPTION OF THE DRAWINGS

The various objects, advantages and novel features of the invention will be more readily appreciated from the following detailed description when read in conjunction with the appended drawing figures, in which.

Throughout the drawings, like reference numbers will be understood to refer to like parts and components.

DETAILED DESCRIPTION OF THE PREFERRED EMBODIMENT

Figure 1:
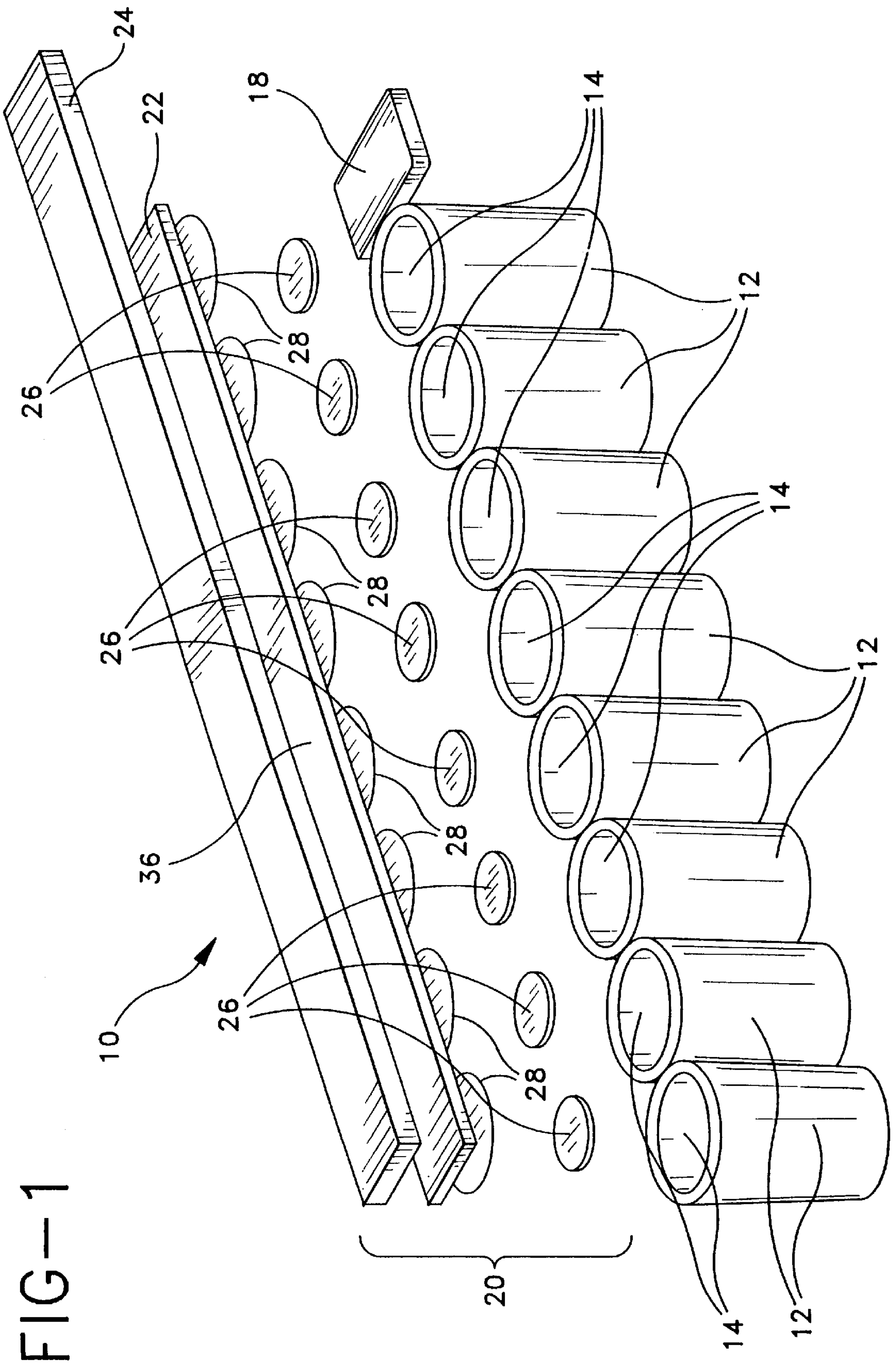
FIG. 1 is an exploded perspective view which illustrates the principal components of an apparatus for carrying out a phage-based antibiotic susceptibility test in accordance with a preferred embodiment of the present invention.

An apparatus 10 for carrying out a phage-based antibiotic susceptibility test on one or more liquid biological samples is illustrated in the exploded view of FIG. 1. The apparatus includes a plurality of sample wells 12, of which there are eight in the preferred embodiment, joined together in a linear or tandem arrangement as shown. Each sample well 12 has a generally upright cylindrical configuration, with an open top 14 and a closed bottom. Adjacent sample wells 12 are joined to each other by connecting regions 16 located near the upper edges of the sample wells 12, and the rearmost sample well 12 is formed with an indexing tab 18 which allows the user to distinguish one end of the row of sample wells 12 from the other. Preferably, the sample wells 12 are made of a transparent, translucent or opaque molded plastic material (such as polystyrene) with the connecting regions 16 and the tab 18 formed integrally with the sample wells 12 themselves.

In addition to the row of sample wells 12, the apparatus 10 comprises a cap strip assembly 20 which includes a molded plastic strip 22 (which is preferably transparent or translucent for reasons to be discussed shortly), a flexible magnetic strip 24, and a series of metal carrier disks 26 equal in number to the sample wells 12 (i.e., eight in the illustrated embodiment). On the lower surface of the cap strip 22 are eight integral stopper-type caps 28, which are spaced apart by a distance corresponding to the spacing between successive sample wells 12. The caps 28 are tightly receivable in the open tops 14 of the sample wells 12 by means for a friction or interference fit, and serve to seal the sample wells 12 during use of the apparatus 10. As will be described in more detail shortly, the metal carrier disks 26 carry on their lower surfaces the dried phage material to be used in the antibiotic susceptibility test, and are magnetically held on the lower interior surfaces of the caps 28 by magnetic attraction to the flexible magnetic strip 24. In the assembled condition of the cap strip assembly 20, the flexible magnetic strip 24 is in contact with the upper surface of the cap strip 22 and the metal carrier disks are in contact with the undersides of the respective caps 28. The flexible magnetic strip 24 has a width approximately equal to that of the cap strip 22, but has a length which is somewhat greater than that of the cap strip 22 to provide an extension or overhang which extends beyond the tab 18 in FIG. 1. This extension facilitates grasping and removal of the flexible magnetic strip 24 by the user during the phage-based antibiotic susceptibility test, as will be described below.

Figure 2:
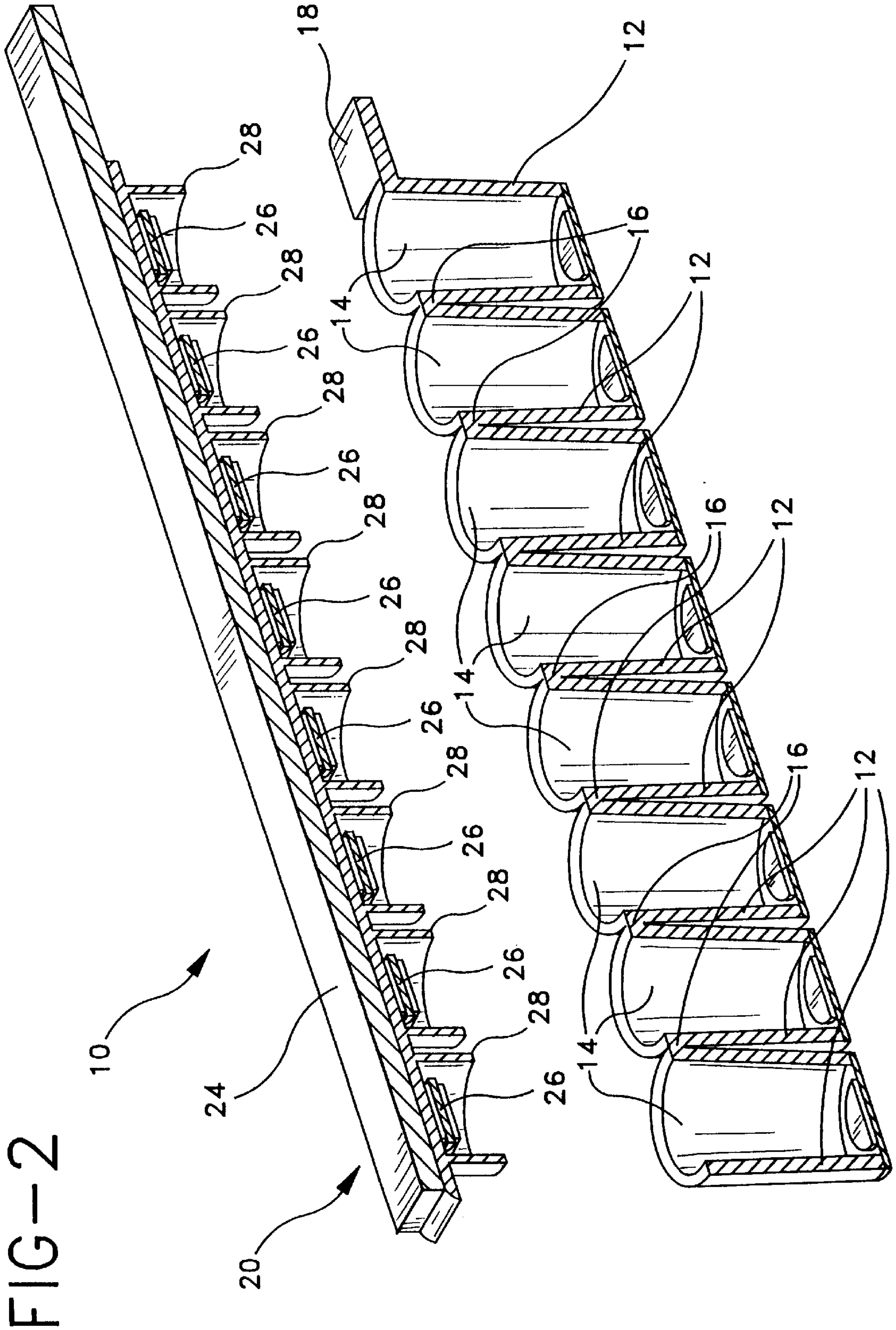
FIG. 2 is an exploded cross-sectional view of the apparatus of FIG. 1, shown partially assembled and ready for use.
Figure 3:
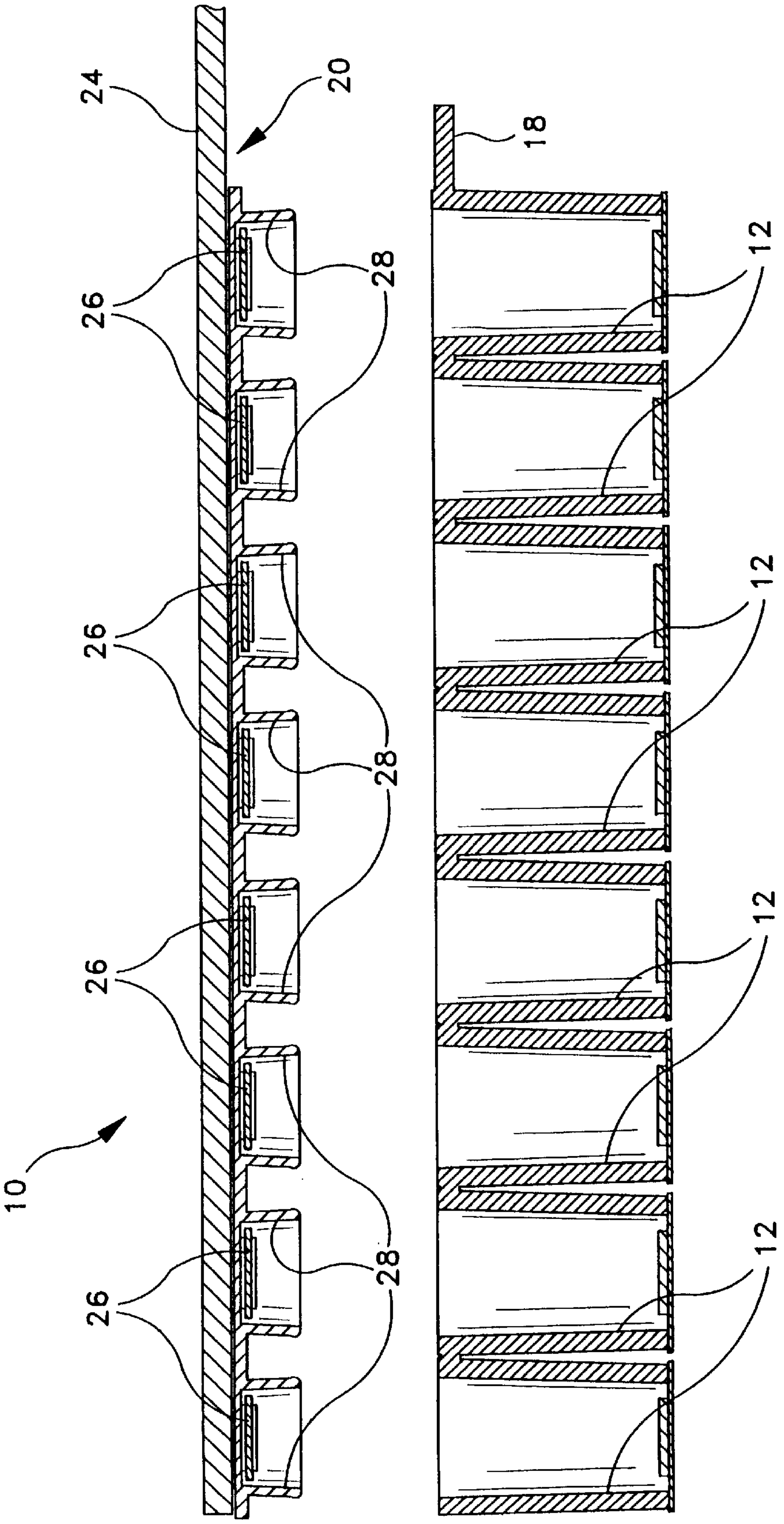
FIG. 3 is a cross-sectional side view of the apparatus of FIG. 1, also shown partially assembled and ready for use.

FIGS. 2 and 3 illustrate the apparatus 10 of FIG. 1 with the cap strip assembly 20 shown fully assembled. The apparatus 10 is shown in FIGS. 2 and 3 as it would appear just prior to the start of a phage-based antibiotic susceptibility test. As noted previously, the flexible magnetic strip 24 is in contact with the flat upper surface of the cap strip 22, and the magnetic attractive force exerted by the flexible magnetic strip 24 retains the metal carrier disks 26 in contact with the undersides of the respective caps 28. In this way, each metal carrier disk 26 (and the dried phage carried thereby) will be within the interior of the respective sample well 12 when the cap 28 is received in the top opening 14. Removal of the flexible magnetic strip 24 from the cap strip 22 will then cause the metal carrier disks 26 to fall into the bottom portions of the respective sample wells 12, thereby mixing the dried phage with the liquid biological samples contained in the sample wells 12. It will be appreciated that the use of stopper-type caps 28 (as opposed to screw caps, for example) is advantageous in that it allows all of the caps 28 to be engaged simultaneously with the top openings 14 of the respective sample wells 12, without the need to individually manipulate each cap 28.

Figure 4:
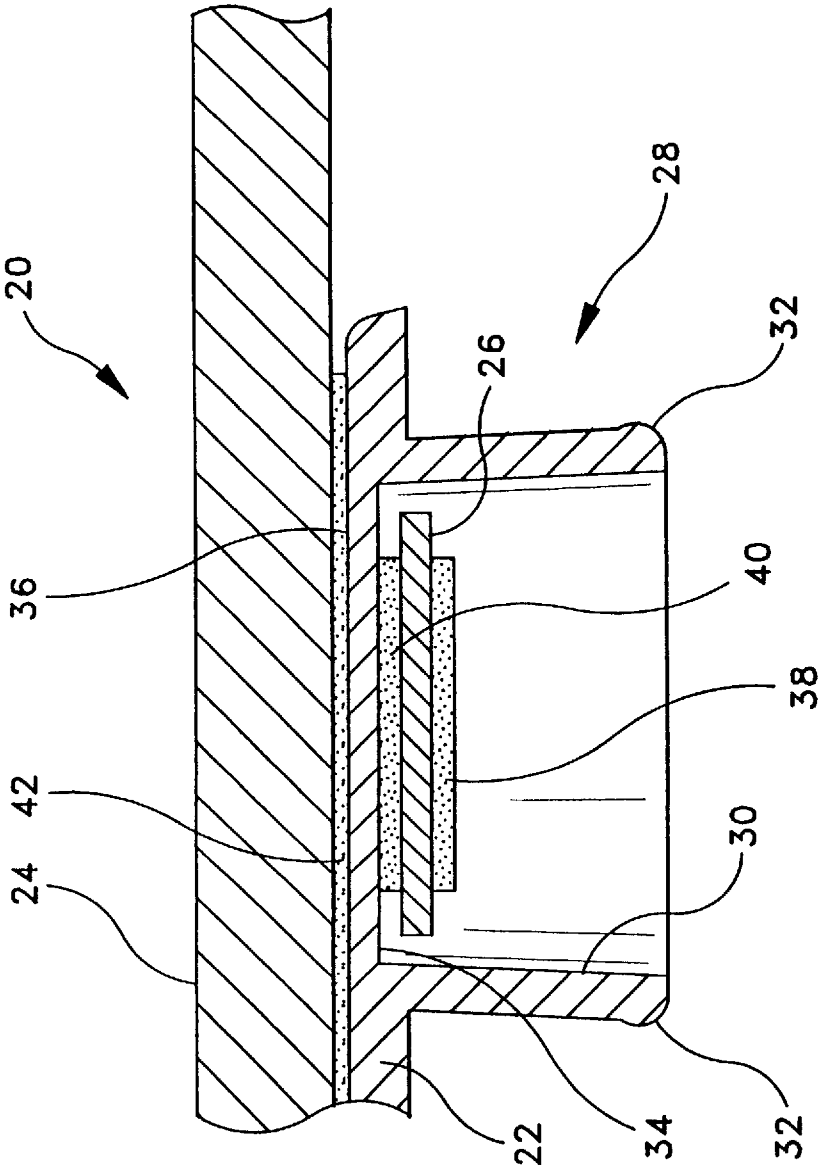
FIG. 4 is an enlarged cross-sectional side view of a portion of the cap strip assembly used in the apparatus of FIG. 1.

The details of the cap strip assembly 20 in the apparatus 10 of FIGS. 1–3 are illustrated in the enlarged view FIG. 4, which is confined to the region of the rightmost cap 28 for simplicity. The cap strip 22 and caps 28 are preferably molded integrally from a suitable transparent or translucent plastic material, such as polypropylene. Each cap 28 includes downwardly-extending cylindrical or annular walls 30 which incline slightly outward from top to bottom, with a rounded or radiused protrusion 32 formed along the bottom outside edge of the walls 30 to form a seal with the internal walls of the corresponding sample well 12. Within the cylindrical cavity defined by the annular walls 30, the metal carrier disk 26 is held in proximate contact with the upper interior surface 34 of the cap. The surface 34 corresponds to the underside of the top surface 36 of the cap 28 and cap strip 22. A layer of the dried phage 38 used in the antibiotic susceptibility test is adhered to the lower surface of the carrier disk 26, as shown. Adhered to the upper interior surface 34 of the cap 28, and interposed between the carrier disk 26 and the surface 34, is a further layer 40 which comprises the Luciferin substrate used in the antibiotic susceptibility test. When the metal carrier disk 26 is in proximate contact with the upper interior surface 34 of the cap 28, as shown in FIG. 4, the metal carrier disk 26 substantially covers the Luciferin substrate layer 40. The term "proximate contact" is used herein to make it clear that the metal carrier disk 26 need not be in physical abutting contact with the upper interior surface 34 of the cap 28 (although it may be), but may instead be separated from the surface 34 by intermediate layers or structures such as the Luciferin substrate layer 40 of FIG. 4. The layers of dried phage 38 and Luciferin substrate 40 may be prepared using a trehalose drying process as disclosed in copending U.S. patent application Ser. No. 081213,304, filed on Mar. 14, 1994, which is incorporated herein by reference.

With continued reference to FIG. 4, the flexible magnetic strip 24 is in proximate contact with the top surface 36 of the caps 28 and cap strip 22. The lines of magnetic flux emanating from the flexible magnetic strip 24 pass through the caps 28 and cap strip 22, and serve to retain the metal carrier disks 26 against the upper interior surfaces of the caps 28 as shown. Preferably, a layer of pressure-sensitive adhesive 42 is interposed between the flexible magnet 24 and the upper surface 36 of the caps 28 and cap strip 22. This prevents inadvertent removal of the flexible magnetic strip 24 from the cap strip 22 until it is actually desired to separate the metal carrier disks 26 from the upper interior surfaces of the caps 28 during the course of an antibiotic susceptibility test. At that point, the flexible magnetic strip 24 is grasped at its free end and stripped or peeled from the cap strip 22. The pressure-sensitive adhesive 42 is preferably selected to allow this to be done manually without exerting a great deal of force. As before, the term "proximate contact" has been used to indicate that the flexible magnetic strip 24 and cap strip 22 need not be in physical abutting contact (although they may be), but may instead be separated by intermediate structures or layers such as the adhesive layer 42. It will be appreciated that the adhesive layer 42 may be omitted if desired, since the magnetic attraction between the flexible magnetic strip 24 and the metal carrier disks 26 may itself be sufficient to hold the flexible magnetic strip 24 in place on the top surface 36 of the cap strip 22.

The flexible magnetic strip 24 is preferably of the well-known type that is often used for so-called "refrigerator magnets" and similar types of novelty items. Extruded flexible magnetic strips of this type are available from Master Magnetics, Inc. of Castle Rock, Colo. as Product No. ZG-38. The flexibility of the magnetic strip 24, while not essential, allows it to be removed more easily from the cap strip 22 during the antibiotic susceptibility test. The metal carrier disks 26 may be made of any ferromagnetic metal, such as steel, and may consist of composite structures rather than solid metal. Examples of such composite structures include metal-coated plastic disks, plastic disks with embedded metal bodies or particles, and so on. It will also be appreciated that roles of the flexible magnetic strip 24 and metal carrier disks 26 may be interchanged, that is, the metal carrier disks 26 may be replaced with magnets and the flexible magnetic strip 24 may be replaced with a flexible metal or composite strip. As a further modification, the strip 24 and carrier disks 26 may both comprise magnets, with opposite poles positioned adjacent to each other. The top surface of the flexible strip 24 may be imprinted with a company logo or product name, instructions for use of the apparatus 10, or other printed information, either on the strip 24 directly or on a separate layer (not shown) adhered to its upper surface.

Figure 5:
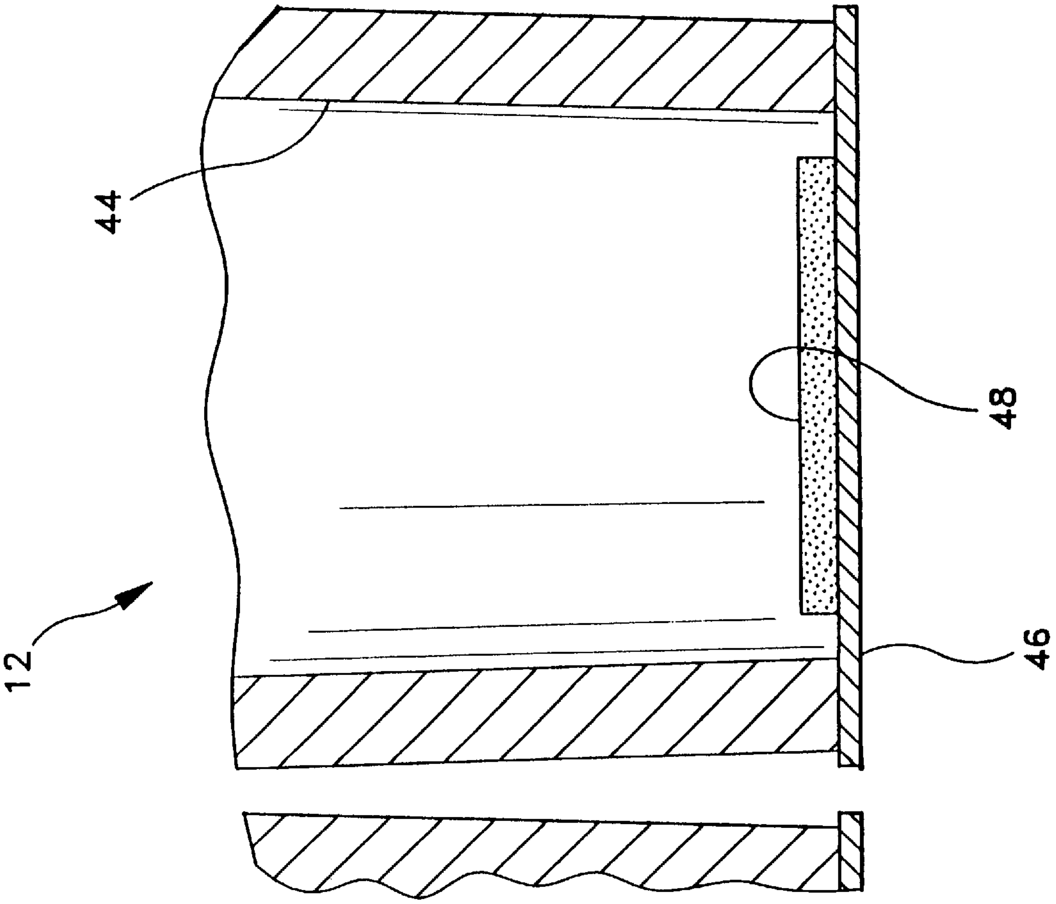
FIG. 5 is an enlarged cross-sectional side view of the bottom portion of one of the connected sample wells used in the apparatus of FIG. 1.

FIG. 5 illustrates the construction of the bottom or lower portion of one of the sample wells 12. The cylindrical side walls 44 of the sample wells taper slightly inwardly from top to bottom a shown. The bottom of each sample well 12 is closed off by a separate bottom wall 46 which preferably comprises a polyolefin membrane (such as Dupont Tyvek) that is not permeable to bacteria or water, but is permeable to gases such as carbon dioxide and oxygen. This permeability allows various biological and chemical processes to occur within the sample well 12 after it has been sealed by the respective cap 28. A disk-shaped layer of dried antibiotic 48 is adhered to the upper surface of the polyolefin membrane 46. The outer edges of the membrane 16 are bonded to the lower edges of the side walls 44 to seal the bottom portion of the sample well 12. It will be understood that the membrane 16 can be deleted if the sample well 12 is used for biological or non-biological process in which gas transfer is not needed (such as DNA amplification), or if venting of the sample well 12 is provided in some other manner. In these situations, the bottom of the sample well 12 may comprise a solid wall that is made of the same material as, and is preferably integral with, the remainder of the sample well 12.

Figure 6:
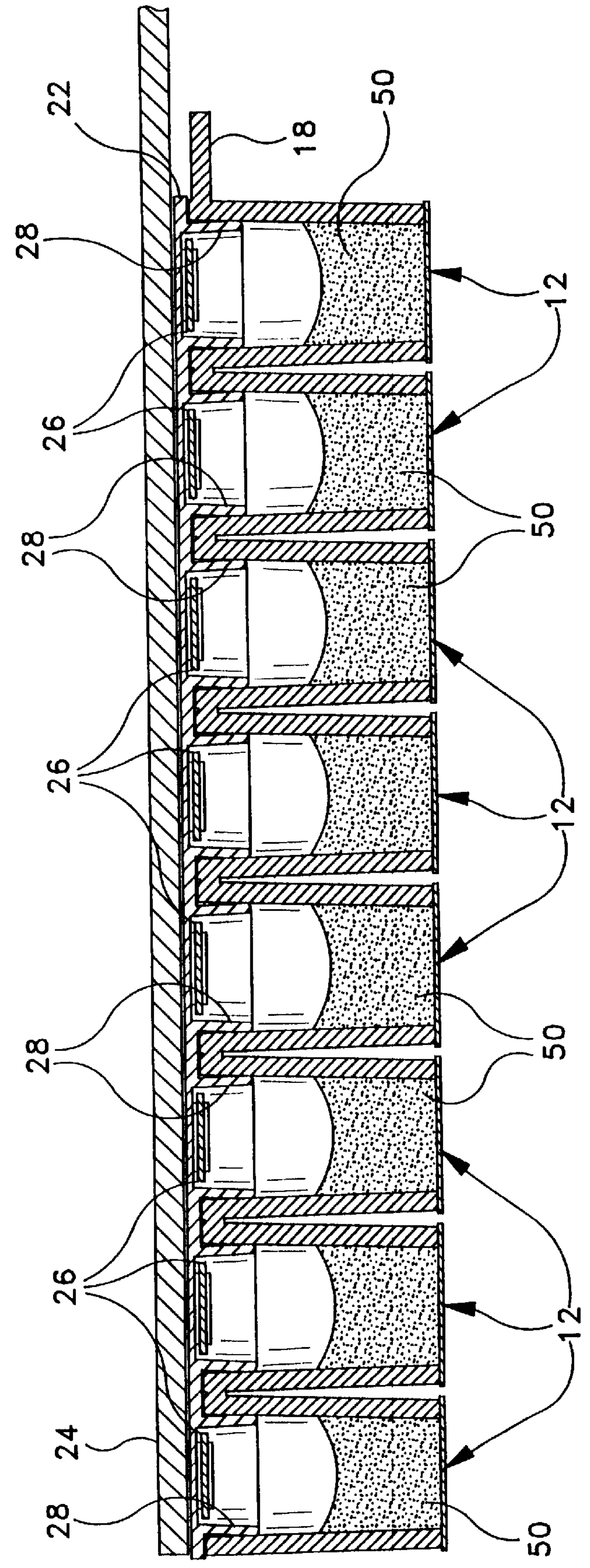
FIG. 6 is a cross-sectional side view of the apparatus of FIG. 1 as it would appear during use, with the cap strip assembly in place and the sample wells filled with liquid biological samples.

FIG. 6 is a cross-sectional view of the assembled apparatus 10 with the cap strip assembly 20 in place on the sample wells 12 and with liquid biological samples 50 contained within the lower portions of the sample wells 12. This is the condition of the apparatus 10 at the start of a phage-based antibiotic susceptibility test. Typically, the various reagents contained in each of the respective sample wells 12 of the apparatus are the same, with the exception of the dried antibiotic layers 48 which are preferably different from one sample well 12 to the next. In addition, the liquid biological samples 50 in each of the sample wells 12 of the apparatus 10 will typically be taken from the same patient, and will ordinarily consist of subdivided parts of a single blood or sputum sample or other body fluid sample taken from the same patient. That being the case, the use of a different antibiotic in each sample well 12 allows the susceptibility of the infectious bacterium contained in the patient sample to several (i.e., up to eight) antibiotics to be tested simultaneously. It is, however, within the scope of the invention to place different patient samples and/or the same antibiotic in two or more of the sample wells 12. It is also within the scope of the invention to carry out biological processes other than phage-based antibiotic susceptibility tests within the sample wells 12, or to carry out processes of a non-biological nature within the sample wells 12.

Figure 7A:
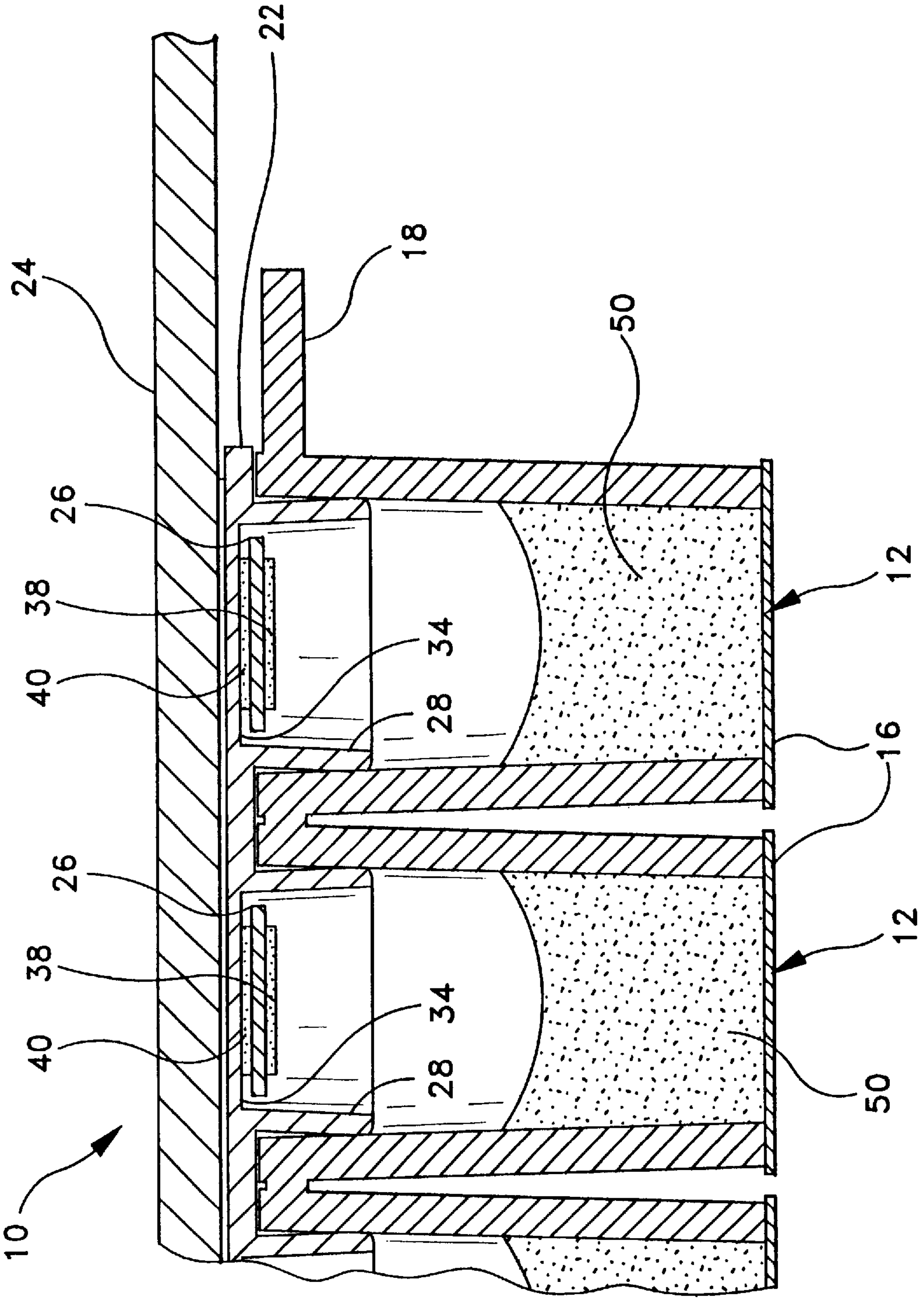
FIGS. 7A–7D are enlarged cross-sectional side views of two adjoining sample wells in the apparatus of FIG. 1, illustrating the sequence of operations involved in performing a phage-based test for antibiotic susceptibility.

FIGS. 7A–7D are enlarged views of two adjoining sample wells 12 in the sealed apparatus 10 of FIG. 6, illustrating the sequence of operations that is carried out during a phage-based antibiotic susceptibility test. In FIG. 7A, the sample wells 12 are in the condition shown in FIG. 6, with the liquid biological samples 50 having been introduced into the sample wells 12 and the caps 28 carried by the cap strip 22 having been inserted into the top openings 14 to seal the sample wells 12 from the ambient atmosphere. The liquid biological samples 50 have dissolved the dried antibiotic 48 at the bottom of each sample well 12, with the result that each antibiotic is now suspended in, or mixed with, a portion of the patient sample. At this point, the apparatus 10 will typically be incubated at a suitable temperature, such as 37° C., for one to two days to allow the bacteria to grow in the presence of the various antibiotics. During this interval, the metal carrier disks 26 remain in proximate contact with the undersides of the caps 28 as a result of the magnetic force exerted by the flexible magnetic strip 24.

Figure 7B:
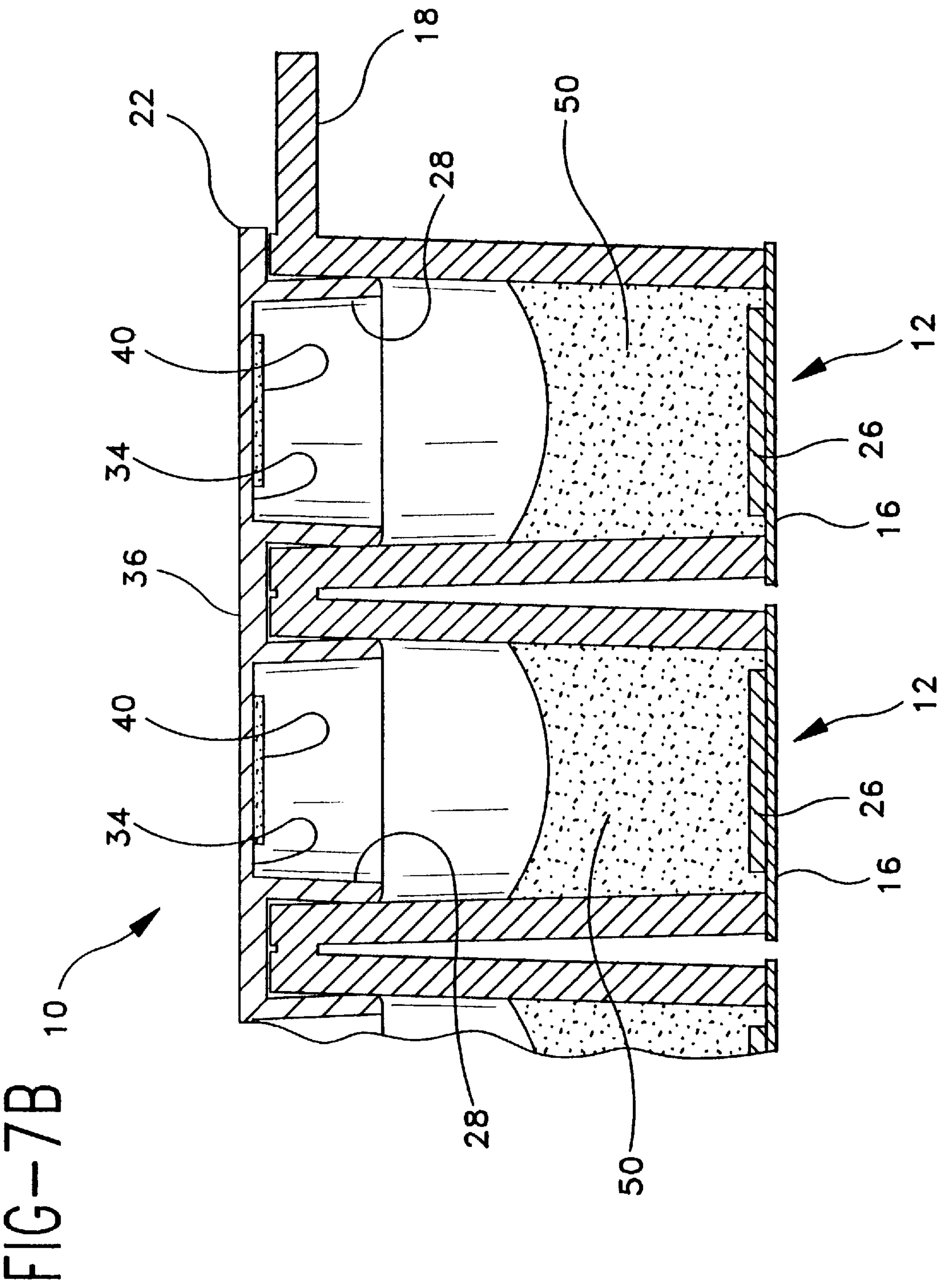
Figure 7C:
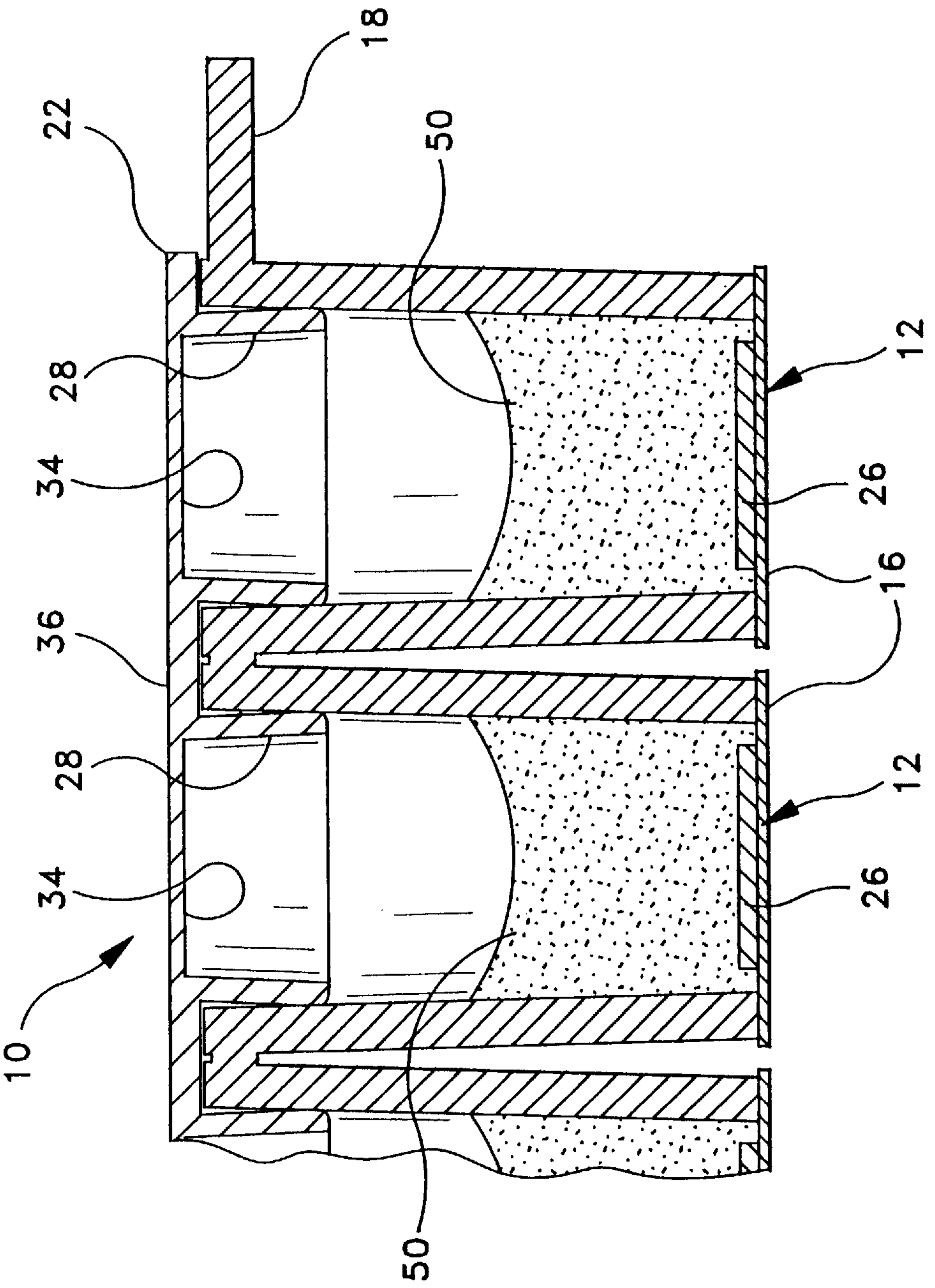

After the liquid biological samples have been incubated for the desired period of time, the dried phage 38 is added to the samples. This is accomplished by manually peeling or stripping the flexible magnetic strip 24 from the top surface 36 of the caps 28 and cap strip 22, against the holding force exerted by the pressure sensitive adhesive 42 and the magnetic attraction between the strip 24 and carrier disks 26. Removal of the flexible magnetic strip 24 eliminates the magnetic holding force on the metal carrier disks 26, with the result that all of the metal carrier disks 26 fall essentially simultaneously into the liquid biological samples 50 contained in the bottom or lower portions of the sample wells 12. When this occurs, the dried phage 38 adhered to the metal carrier disks 26 is dissolved by, and mixes with, the liquid biological samples 50. This is illustrated in FIG. 7B, in which the flexible magnetic strip 24 has been removed and the metal carrier disks 26 are resting at the bottom of the sample wells 12 on top of the membranes 16. The dissolved phage is then incubated with the liquid biological samples 50 for a suitable period of time, typically one or more hours.

Figure 7D:
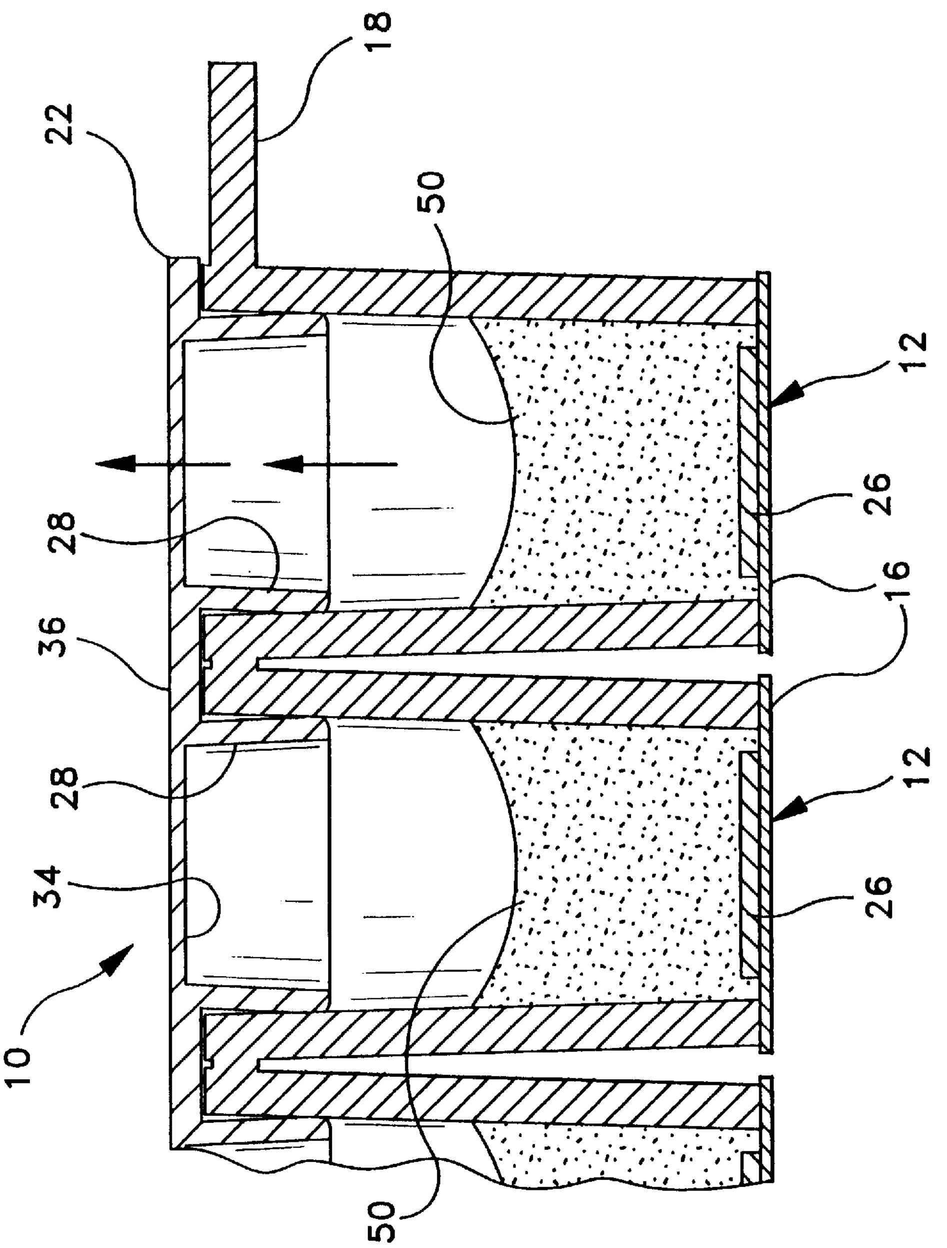

Following the phage incubation period, the Luciferin substrate 40 that is adhered to the underside of the caps 28 is mixed with the liquid biological sample 50. This is accomplished by either shaking or inverting the apparatus 10, or both, to bring the liquid biological samples 50 into contact with the dried Luciferin substrate 40. This causes the liquid biological samples 50 to dissolve the Luciferin substrate 40, leaving the apparatus in the condition shown in FIG. 7C. The metal carrier disks 26, which are now free to move within the sample wells 12, serve as agitators to promote mixing between the samples 50 and the Luciferin substrate 40 during shaking or inversion of the apparatus 10. In FIG. 7D, a detection step is carried out by detecting any luninescence in the liquid biological samples caused by the combination of Luciferase (produced by live bacteria) with the Luciferin substrate. In order to avoid the need to open or unseal the sample wells 12 during the detection step, the caps 28 and cap strip 22 are preferably made either transparent or translucent, as noted earlier, so that any luminescence produced by the liquid biological samples 50 can be detected from the top of the sealed assembly 10. An automated instrument such as a luminometer is preferably used in the detection step, but the detection step can also be carried out manually if desired. In the example shown in FIG. 7D, the luminescence produced by the rightmost sample well 12 indicates that the bacteria in the liquid biological sample 50 are still alive, and hence that the antibiotic used in that sample well 12 was not effective to kill the bacteria. The lack of luminescence in the adjacent sample well 12 indicates that the bacteria in that sample well 12 are no longer viable, and hence that the antibiotic used in that sample well is effective against the particular bacterium in the patient sample. Similar results (i.e., either luminescence or non-luminescence) will be produced by the remaining sample wells 12 of the apparatus 10.

In an exemplar embodiment, the apparatus 10 of FIGS. 1–7 may have a length of about 3.5 inches (including the overhang portion of the flexible magnetic strip 24), a width of approximately 0.35 inch, and a height of approximately 0.6 inch. The individual sample wells may have a height of approximately 0.5 inch and an outside diameter ranging from about 0.35 inch at the top to approximately 0.32 inch at the bottom, with a wall thickness of approximately 0.04 inch. The wall thickness of the caps 28 and cap strip 22 may be approximately 0.03 inch. It will be understood that these dimensions are merely exemplary and that the size of the apparatus 10 and its various individual parts may be changed to suit the requirements of particular applications. It will also be understood that the apparatus 10 may be used singly or in groups, and in the latter case a plurality of apparatus 10 (typically 12) may be carried in a tray or holder for more convenient handling in the laboratory.

A modified embodiment of the apparatus 10, not illustrated in the drawings, may include an integral, upwardly extending lip or flange extending along each longitudinal edge of the cap strip 22 to define a track for retaining the magnetic strip 24 in contact with the surface 36 while allowing the strip 24 to slide longitudinally along the length of the cap strip 22. This may avoid any need for the adhesive layer 42, and may also avoid any need for flexibility in the magnetic strip 24 since the strip can be removed by longitudinal sliding between the lips or flanges rather than by being peeled or stripped from the surface 36. However, the embodiment illustrated in FIGS. 1–7 is preferred since it is simpler in construction, and, given the absence of the lips or flanges, is slightly shorter in height. This latter advantage may be helpful in allowing the apparatus 10 to fit within existing types of luminometers.

From the foregoing description, it will be appreciated that the apparatus 10 allows a complete phage-based antibiotic susceptibility test to be performed on a patient sample, consisting of live infectious organisms, while the sample is maintained in a sealed unit. By maintaining the patient sample in a sealed unit, the sample is rendered safe to handle in an open laboratory. It will be apparent that the principles of the present invention are applicable to other types of biological and non-biological processes in which there is a need to add one or more reagents to a liquid sample while the sample is held in a sealed vessel.

The foregoing is illustrative of the present invention, and is not to be construed as limiting thereof, as numerous alternatives to the devices and methods described which incorporate the present invention will be apparent to those skilled in the art. The invention is accordingly defined by the following claims with equivalents of the claims to be included therein.

That which is claimed is:

1. A method for adding a reagent to a sample, comprising:

placing said sample into a first portion of a sample well;

placing said reagent into a second portion of said sample well located above said first portion without contact between said reagent and said sample;

sealing said sample well with said sample and said reagent therein;

retaining said reagent in said first portion of said sealed sample well by magnetic force; and releasing said magnetic force to allow said reagent to fall into said second portion of said sealed sample well and mix with said sample.

2. The method claimed in claim 1, further comprising:

before sealing said sample well, placing a second reagent into said second portion of said sample well without contact with said sample;

after releasing said magnetic force to allow said reagent to fall into said second portion of said sealed sample well and mix with said sample, mixing said second reagent with said sample by shaking or inverting said sample well.

3. The method claimed in claim 2 wherein:

said sample is subjected to a biological process comprising a test for the susceptibility of a bacterium in said sample to an antibiotic;

said reagent comprises a bacteriophage which induces luciferase production by said bacterium; and said second reagent comprises luciferase.

* * * * *